(12) United States Patent
Perouse (10) Patent No.: US 8,512,634 B2
(45) Date of Patent: Aug. 20, 2013

(54) INSTALLATION FOR STERILISATION OF A PLURALITY OF OBJECTS AND ASSOCIATED STERILISATION METHOD

(75) Inventor: Eric Perouse, Ivry le Temple (FR)

(73) Assignee: PE Investissement, Ivy le Temple (FR)

( * ) Notice: Subject to any disclaimer, the term of this patent is extended or adjusted under 35 U.S.C. 154(b) by 405 days.

(21) Appl. No.: 12/833,655

(22) Filed: Jul. 9, 2010

(65) Prior Publication Data
US 2011/0008208 A1 Jan. 13, 2011

(30) Foreign Application Priority Data
Jul. 10, 2009 (FR) .................................. 09 54838

(51) Int. Cl.
*A61L 9/00* (2006.01)

(52) U.S. Cl.
USPC .......................................... 422/30; 422/292

(58) Field of Classification Search
USPC .................................... 422/30, 292
See application file for complete search history.

(56) References Cited

U.S. PATENT DOCUMENTS

| 6,323,473 | B1 * | 11/2001 | Yamamoto et al. ........... 219/771 |
| 2002/0119074 | A1 | 8/2002 | McGowan, Jr. |

FOREIGN PATENT DOCUMENTS

| EP | 0624518 A2 | 11/1994 |
| GB | 2326817 A | 1/1999 |
| WO | 2007/000639 A1 | 1/2007 |

* cited by examiner

*Primary Examiner* — Kevin Joyner
(74) *Attorney, Agent, or Firm* — Sughrue Mion, PLLC (57) ABSTRACT

An installation which includes an input station, a sterilization station which includes a sterilization chamber, a desorption station which includes a desorption chamber, and an output station. The installation includes a transporting element which is for transporting multiple objects and which is capable of successively moving the objects from the input station into the sterilization station and into the desorption station as far as the discharge station. The transporting element includes a continuous guiding path, a guide device which is guided by the guiding path. The guided device includes a movement mechanism which is capable of moving the objects between a position for movement along the guiding path and a position for insertion of the objects in the sterilization chamber and the desorption chamber.

14 Claims, 4 Drawing Sheets

INSTALLATION FOR STERILISATION OF A PLURALITY OF OBJECTS AND ASSOCIATED STERILISATION METHOD

CROSS REFERENCE TO RELATED APPLICATIONS

This application claims the benefit of French Patent Application No. 0954838, filed Jul. 10, 2009, the disclosure of which is incorporated herein by reference.

The present invention relates to an installation for sterilising a plurality of objects, of the type comprising:
- an input station which is capable of receiving the plurality of objects to be sterilised;
- a sterilisation station which comprises at least one sterilisation enclosure which is intended to receive the plurality of objects, the sterilisation station comprising at least one means for introducing a sterilising fluid into the sterilisation enclosure and at least one means for discharging the sterilising fluid;
- a desorption station comprising at least one desorption enclosure, the desorption station comprising at least one means for draining the desorption enclosure;
- an output station which is capable of receiving the plurality of objects after sterilisation;
- means which are for transporting the plurality of objects and which are capable of successively moving the plurality of objects from the input station into the sterilisation station and into the desorption station as far as the unloading station.

Such an installation is used for sterilising medical devices which are intended to come into contact with a surface of a patient's body. Those medical devices are, for example, medical, surgical or dental tools, injection syringes or removal syringes, catheters or implants, such as vascular prostheses, implantable chambers and more generally medical devices in contact with the human body or an animal's body.

The installation is configured to sterilise a large number of medical devices simultaneously in order to comply with the applicable standards for reliable and safe use of those devices.

A known installation of the above-mentioned type generally comprises an input station, in which pallets of medical devices to be sterilised are unloaded.

The installation further comprises a pre-processing station, in which the medical devices contained in the pallets are subjected to an atmosphere which is controlled in terms of hygrometry and temperature for a period of time of from 8 to 12 hours.

The installation then comprises a sterilisation station which is provided with a sterilisation enclosure which is generally formed by an autoclave having a large volume.

In that enclosure, the medical devices are placed in contact with a sterilising gas, such as ethylene oxide, for a period of time, for example, of 8 hours.

The installation further comprises a desorption station which is provided with desorption enclosures where the medical devices are subjected, for a period of time of from 16 to 32 hours, to desorption in order to remove the residual ethylene oxide.

Therefore, such an installation is very extensive, particularly when the number of medical devices to be processed is large. The time for processing each batch of devices is high which requires a large amount of space to store the batches between two stations.

Furthermore, in order to move from one station to another, the medical devices contained in pallets are transported by fork-lift vehicles from the input station as far as the pre-processing station, from the pre-processing station to the sterilisation station, from the sterilisation station to the desorption station and finally from the desorption station to the output station.

Therefore, such an installation necessitates, when the number of pallets to be processed is large, a large number of handling operations which is expensive and makes substantial human resources necessary.

Furthermore, great precautions must be taken to prevent the operators from being exposed to the sterilising gases which are sometimes irritating or toxic.

Finally, this type of installation does not ensure that medical devices are transported from the pre-processing step to the desorption station without passing via the sterilisation station, which may be potentially dangerous. In order to overcome this risk, it is necessary to construct sealed partitions between all the stations which is expensive and troublesome.

Therefore, an object of the invention is to obtain a sterilisation installation which is capable of processing a large number of objects to be sterilised in a manner which is inexpensive, very safe for the operators and very reliable.

To that end, the invention relates to a sterilisation installation of the above-mentioned type, characterised in that the transport means comprise:
- a continuous guiding path, the input station, sterilisation station, desorption station and unloading station being arranged successively opposite the guiding path; and
- at least one device which is guided by the guiding path, the guided device comprising movement means which are capable of moving the plurality of objects relative to the guided device between a position for common movement of the plurality of objects and the guided device along the guiding path and a position for insertion of the plurality of objects in each of the sterilisation enclosure and the desorption enclosure.

The installation according to the invention may comprise one or more of the following features, taken in isolation or in accordance with any technically possible combination:
- it comprises at least one container which delimits a volume for receiving the plurality of objects, the container comprising at least one member for releasable connection to the movement means;
- the guiding path is located above the sterilisation enclosure and above the desorption enclosure, the sterilisation enclosure and the desorption enclosure opening upwards opposite the guiding path;
- the guided device comprises a travelling platform, the movement means comprising at least one traction member which is carried by the travelling platform and which is capable of lowering the plurality of objects into the sterilisation enclosure and into the desorption enclosure, and of raising the plurality of objects in order to remove them from the sterilisation enclosure and the desorption enclosure;
- the sterilisation enclosure and the desorption enclosure each delimit a single access opening for inserting and removing the plurality of objects;
- the guiding path extends linearly between the input station and the output station, the sterilisation station and the desorption station being located side by side along the guiding path between the input station and the output station;
- the sterilisation station comprises a plurality of sterilisation enclosures, the desorption station comprising a plurality of desorption enclosures, the sterilisation enclosures and the desorption enclosures being arranged successively side by side in an adjacent manner along the guiding path;

it comprises a pre-processing station which is arranged upstream of the sterilisation station along the guiding path, the pre-processing station comprising at least one pre-processing enclosure and means for controlling the humidity and/or the temperature in the pre-processing enclosure;

it comprises a confinement wall which delimits a confinement volume, the sterilisation station and the desorption station being located in the confinement volume, the input station and the output station being located outside the confinement volume, and the confinement wall delimits an upstream lock chamber and a downstream lock chamber opening in the confinement volume, the guiding path extending successively through the upstream lock chamber, the confinement volume and the downstream lock chamber;

the output station comprises at least one moving vehicle which delimits a surface for loading the plurality of sterilised objects, the moving vehicle being movable between a position for receiving the plurality of objects, in which the loading surface extends opposite the guiding path in order to be loaded by the transport means, and a position remote from the guiding path;

the sterilisation enclosure delimits a sterilisation chamber which is capable of receiving the plurality of objects and comprises a lid for sealingly closing the sterilisation chamber, the sterilisation station comprising means for moving the lid which are capable of moving the lid between a position for access to the sterilisation chamber and a position for closing the sterilisation chamber;

in the access position, the sterilisation chamber opens opposite the guiding path, the lid being transversely displaced relative to the guiding path; and the means for moving the lid comprise an auxiliary device which is guided by the guiding path.

The invention further relates to a method for sterilising a plurality of objects in an installation as defined above, characterised in that it comprises the following steps:

the plurality of objects being taken from the input station by the movement means carried by the guided device;

moving the guided device over the guiding path in order to place it opposite the sterilisation station;

the plurality of objects being introduced into the sterilisation enclosure by the movement means carried by the guided device;

injecting sterilising fluid into the sterilisation enclosure in order to sterilise the plurality of objects in the sterilisation enclosure;

the plurality of objects being removed from the sterilisation enclosure by the movement means carried by the guided device;

moving the guided device over the guiding path in order to place it opposite the desorption station;

the plurality of objects being introduced into the desorption enclosure by the movement means carried by the guided device;

desorption of the sterilising fluid from the plurality of objects in the desorption enclosure;

the plurality of objects being removed from the desorption enclosure by the movement means carried by the guided device;

moving the guided device over the guiding path as far as the output station;

the plurality of sterilised objects being deposited in the output station by the movement means carried by the guided device.

The invention will be better understood from a reading of the following description which is given purely by way of example and with reference to the appended drawings, in which.

A first sterilisation installation 10 according to the invention is illustrated in FIGS. 1 to 4.

That installation 10 is intended to sterilise a plurality of objects which are advantageously formed by medical devices which are capable of coming into contact with a surface of a patient's body.

Those medical devices are, for example, medical, surgical or dental tools, injection syringes or removal syringes, catheters, implants, such as vascular prostheses, implantable chambers.

Those objects are advantageously contained in boxes, the boxes themselves being stored in pallets 12 which are visible in FIGS. 1 to 5. Each pallet 12 generally contains more than 10 objects, or more than approximately 100 objects.

Figure 1:
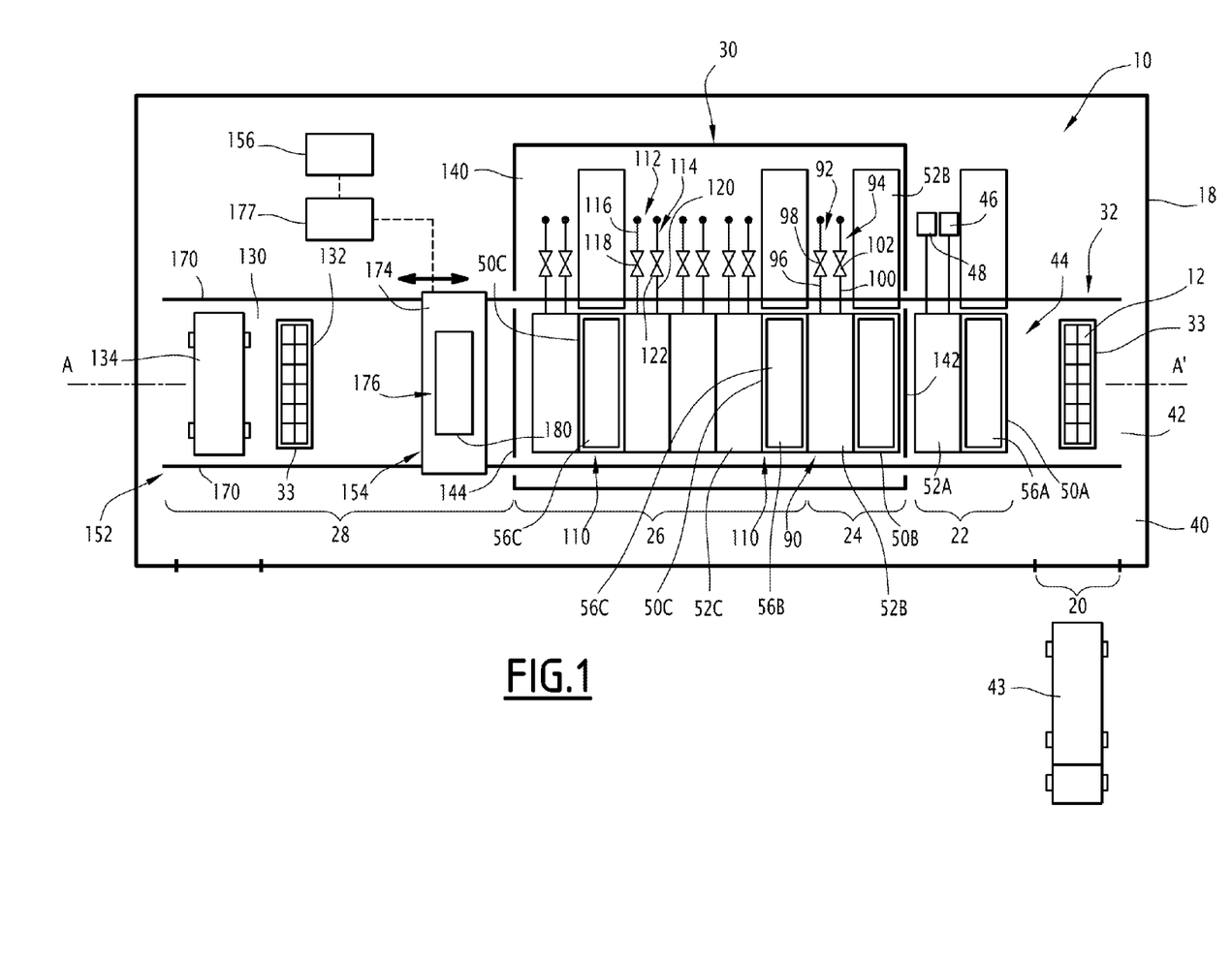
FIG. 1 is a schematic top view of a first installation according to the invention.

In the example illustrated in FIG. 1, the first sterilisation installation 10 is arranged in a single building 18.

It comprises, in a downstream direction, along a horizontal movement axis A-A' of the objects, an input station 20, for receiving the pallets 12 containing objects to be sterilised, a pre-processing station 22, a sterilisation station 24 and a desorption station 26.

It further comprises an output station 28 for receiving the pallets 12 of sterilised objects and conveying them to a storage location or a location for use.

The installation 10 further comprises a confinement wall 30 of the sterilisation station 24 and the desorption station 26, and means 32 for transporting the pallets 12 of objects successively through the stations 20 to 28, the transport means 32 comprising at least one container 33 for simultaneously handling a plurality of pallets 12.

The input station 20 comprises an unloading platform 40 for receiving the pallets 12 of objects to be sterilised from outside the building 18 and an input plate 42, on which the pallets 12 are placed in a container 33 in order to be taken up by the transport means 32.

In that example, the platform 40 is suitable for receiving at least one lorry 43 which contains pallets 12 of non-sterile objects. The plate 42 comprises a horizontal abutment surface for the pallets 12 and the container 33.

The pre-processing station 22 comprises at least one pre-processing enclosure 44, means 46 for adjusting the temperature in the enclosure 44 and means 48 for adjusting the hygrometry in the chamber 44.

In the example illustrated in FIG. 1, the pre-processing station 22 comprises two identical enclosures 44 which are located side by side in an adjacent manner. The enclosures 44 extend substantially perpendicularly relative to the movement axis A-A'.

Figure 2:
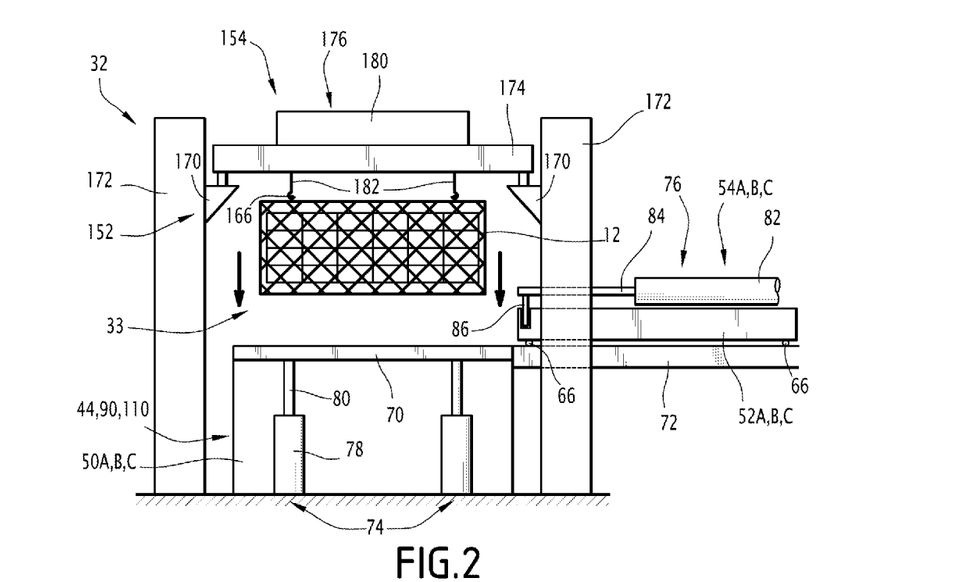
FIG. 2 is a partial side view of a station of the installation of FIG. 1, when a container which receives a plurality of objects is being loaded in the station.

As illustrated in FIG. 2, each enclosure 44 comprises a pre-processing vessel 50A, a lid forming a removable cover 52A and means 54 for moving the removable cover 52A between a position for closing the vessel 50A and a position for access to the vessel 50A.

The vessel 50A is of substantially parallelepipedal, elongate form in accordance with an axis perpendicular to the axis A-A'. It delimits a pre-processing chamber 56A which opens upwards via an upper opening 58.

The upper opening 58 is delimited at its periphery by an upper edge 60 of the vessel 50A. The edge 60 receives the cover 52A in abutment in its closure position.

The edge 60 carries a sealing joint 62 which extends at the periphery of the upper opening 58 in order to ensure the sealing through the upper opening 58 when the cover 52A closes the upper opening 58.

The chamber 56A is of substantially parallelepipedal form similar to that of the container 33. The volume of the pre-processing chamber 56A is slightly greater, for example, a maximum of 20% greater, than the volume of the container 33 which is intended to receive the pallets 12.

That volume is, for example, greater than 1 m$^3$ and is advantageously between 1 m$^3$ and 100 m$^3$.

The cover 52A comprises a closure panel 64 which has a width slightly greater than the width of the vessel 50A. It comprises movement members 66 which are arranged along the lateral edges of the panel 64 on a lower surface of the panel 64.

Figure 3:
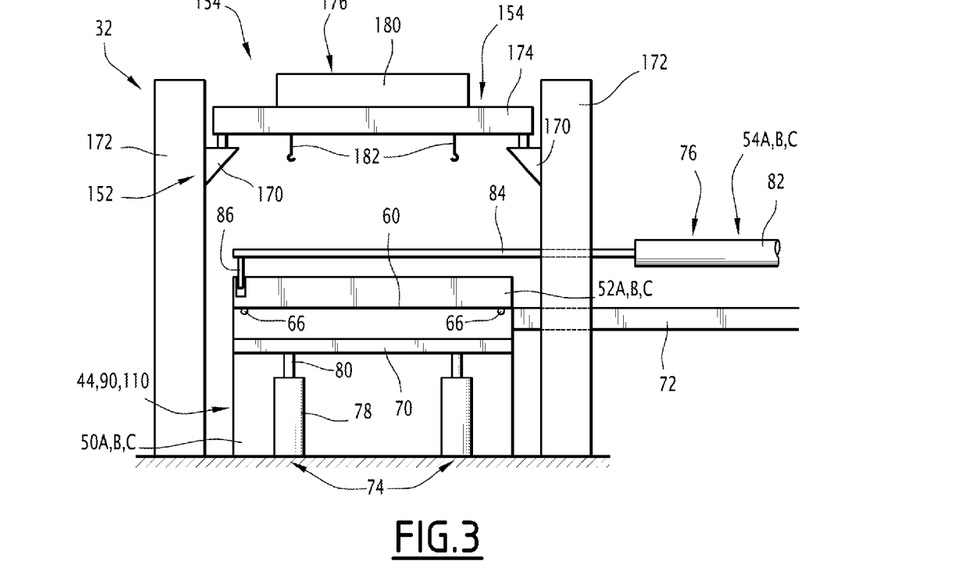
FIG. 3 is a view similar to FIG. 2 during the processing of the plurality of objects in the station.
Figure 4:
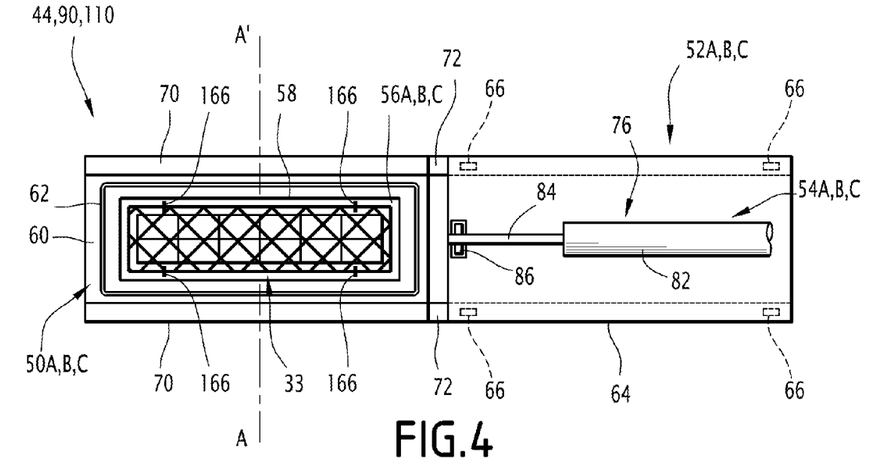
FIG. 4 is a top view of the relevant portions of the station illustrated in FIG. 2.

The cover 52A is transversely movable relative to the axis A-A' between a position for access to the chamber 56A, illustrated in FIGS. 2 and 4, and a closure position illustrated in FIG. 3.

In the access position, the panel 64 has been displaced transversely away from the upper opening 58. The volume located above the upper opening 58 is free over at least the height of a container 33 in order to allow the container 33 containing the pallets 12 to be introduced from above into the pre-processing chamber 56A.

In the closure position, the panel 64 is applied against the upper edge 60. By means of the joint 62, the panel 64 closes in a sealed manner the upper opening 58 in an upward direction and prevents access from outside to the pre-processing chamber 56A.

In the example illustrated in FIG. 2, the movement means 54A comprise movable rails 70 which are arranged laterally along the vessel 50A, fixed rails 72 which are displaced transversely relative to the vessel 50A, first jacks 74 for vertically moving the movable rails 70 and at least a second jack 76 for horizontally moving the cover 52A on the rails 70, 72.

The movable rails 70 extend transversely relative to the axis A-A' at one side and the other of the vessel 50A. They are carried by the first jacks 74.

Each rail 70 is movable under the effect of the first jacks 74 between a lower rest position, illustrated in FIG. 3, and an upper position for moving the cover, illustrated in FIG. 2.

In the lower position, the movable rails 70 are located below the fixed rails 72 and below the edge 60.

In the upper position, each movable rail 70 is located substantially in alignment with the edge 60 opposite the fixed rail 72. The upper surface of each movable rail 70 is flush with the upper surface of a fixed rail 72, those upper surfaces defining a continuous horizontal surface for guiding the movement members 66. The guiding surface extends transversely relative to the axis A-A'.

Each fixed rail 72 extends vertically in alignment with the edge 60, below the second jack 76. The fixed rail 72 further extends transversely away from the vessel 50A.

Each first jack 74 comprises a cylinder 78 and a vertical shank 80 which carries the movable rail 70.

In the example illustrated in FIG. 2, the movement means 54 comprise, for each movable rail 70, two first parallel jacks 74 which carry two transversely spaced-apart locations of the movable rail 70.

The second jack 76 comprises a horizontal cylinder 82 which is arranged above the cover 52A and a horizontal shank 84 which can be deployed by means of the horizontal cylinder 82. The horizontal shank 84 has a free end 86 which is fixed to the cover 52A along a transverse movement axis of the shank 84 whilst allowing relative vertical movement of the cover 52A relative to the shank 84.

In this manner, the horizontal shank 84 is movable between a configuration retracted in the cylinder 82, in which the cover 52A occupies its access position, and a deployed configuration, in which the cover 52A has been moved on the rails 72, 70 opposite the upper opening 58 in order to close that opening 58.

The means 46 for adjusting the temperature are capable of adjusting the temperature in the pre-processing chamber 56A so that the temperature is at a given temperature selected, for example, between 30° C. and 60° C.

The means 48 for adjusting the hygrometry are capable of adjusting the percentage of humidity in the pre-processing chamber 56A to a given value of between 40% and 100% of relative humidity.

The sterilisation station 24 comprises at least one sterilisation enclosure 90 and, for each enclosure 90, means 92 for introducing a sterilising gas into the enclosure 90 and means 94 for draining the enclosure 90.

In the example illustrated in FIG. 1, the sterilisation station 24 comprises two identical enclosures 90.

The enclosures 90 extend transversely relative to the movement axis A-A'. They are positioned side by side in an adjacent manner along the axis A-A'.

At least one sterilisation enclosure 90 extends in a manner adjacent to a pre-processing enclosure 44 of the pre-processing station 22 in order to minimise the space taken up by the installation 10 in the building 18.

The sterilisation enclosure 90 has a structure similar to that of the pre-processing enclosure 44. With reference to FIGS. 1 to 3, the enclosure 90 thus comprises a sterilisation vessel 50B, a cover 52B and means 54B for moving the cover 52B between a position for closing the vessel 50B and a position for access to the vessel 50B.

The vessel 50B internally delimits a sterilisation chamber 56B which opens upwards.

The vessel 50B, the cover 52B and the movement means 54B are structures which are similar to that of the pre-processing vessel 50A, that of the cover 52A and that of the movement means 54A, respectively, which are described above and will not therefore be described in greater detail.

As illustrated in FIG. 1, the means 92 for introducing a sterilising gas comprise a conduit 96 for introducing sterilising gas. The conduit 96 is provided with a control valve 98.

That conduit 96 connects a container (not illustrated) of sterilising gas to the sterilisation chamber 56B. The sterilising gas is advantageously ethylene oxide.

The draining means 94 comprise a draining conduit 100 which is provided with a draining valve 102. The draining conduit 100 opens in the sterilisation chamber 56B. It is connected downstream to a vacuum pump.

The desorption station 26 comprises at least one desorption enclosure 110, means 112 for introducing a flushing gas into the desorption enclosure 110 and means 114 for discharging the desorbed gases.

In the example illustrated in FIG. 1, the station 26 comprises at least two times as many, advantageously at least three times as many desorption enclosures 110 as the sterilisation station 24 comprises sterilisation enclosures 90. In this manner, the number of enclosures 110 illustrated in FIG. 1 is six.

The enclosures 110 extend transversely relative to the movement axis A-A'. They are positioned side by side in an adjacent manner along the axis A-A'.

A desorption enclosure 110 extends in a manner adjacent to a sterilisation enclosure 90 of the sterilisation station 24 in order to minimise the space taken up by the installation 10 in the building 18.

Each desorption enclosure 110 has a structure similar to that of the sterilisation enclosure 90 and pre-processing enclosure 44.

With reference to FIGS. 1 to 3, each enclosure 110 thus comprises a desorption vessel 50C, a cover 52C and means 54C for moving the cover 52C between a position for closing the vessel 50C and a position for access to the vessel 50C.

The vessel 50C internally delimits a desorption chamber 56C which opens upwards. The vessel 50C, the cover 52C and the movement means 54C are structures which are similar to that of the pre-processing vessel 50A, that of the cover 52A and that of the movement means 54A, respectively, which are described above and will not therefore be described in greater detail.

The means 112 for introducing a flushing gas comprise an introduction conduit 116 which is connected to a flushing gas container (not illustrated). The introduction conduit 116 is provided with a control valve 118. The flushing gas is, for example, a neutral gas, such as nitrogen.

The draining means 114 comprise a draining conduit 120 which is provided with a control valve 122, the conduit 120 being connected to a vacuum pump (not illustrated).

The output station 28 comprises an output plate 130 which has a region 132 for storing the pallets 12 of sterilised objects.

In the example illustrated in FIG. 1, the output station 28 further comprises at least one moving vehicle 134 which is intended to receive the pallets 12 of sterilised objects in order to further transport them out of the building 18.

The moving vehicle 134 is, for example, a lorry trailer. The vehicle 134 can thereby be moved between a position for receiving the pallets 12 of objects, in which it extends opposite the transport means 32, and a position remote from the transport means 32, located outside the building 18.

The confinement wall 30 extends around the sterilisation station 24 and the desorption station 26. It surrounds those stations 24, 26 at the periphery thereof and covers them.

The wall 30 delimits an internal confinement volume 140 which has a controlled atmosphere and in which there are provided the sterilisation enclosures 90 and the desorption enclosures 110.

The length of the confinement volume 140 taken along the axis A-A' is further substantially equal to the cumulative length taken up by the sterilisation vessels 50B and the desorption vessels 50C along the axis A-A'.

The confinement wall 30 delimits an upstream lock chamber 142 and a downstream lock chamber 144 for the passage of the transport means 32.

The upstream lock chamber 142 opens above the sterilisation enclosures 90 between the pre-processing station 22 and the sterilisation station 24. It is centred on the movement axis A-A'.

The downstream lock chamber 144 opens opposite the upstream lock chamber 142 along the axis A-A'. It opens between the pre-processing station 26 and the output station 28 above the desorption enclosures 110.

According to the invention, the transport means 32 comprise, in addition to the transport container 33 for the pallets 12, a guiding path 152 which extends linearly along the axis A-A' along the various stations 20 to 28, and a guided device 154 for moving the container 33 between the various stations 20, 28. The device 154 is mounted so as to move on the guiding path 152.

The transport means 32 further comprise means 156 for controlling the movement of the guided device 154.

The container 33 has a shape substantially similar to the shape of the pre-processing chamber 56A, the shape of the sterilisation chamber 56B and the shape of the desorption chamber 56C. In that manner, it is of parallelepipedal form. It delimits an internal volume 160 for receiving the pallets 12 which is capable of receiving, for example, between 2 and 50 pallets 12.

Figure 5:
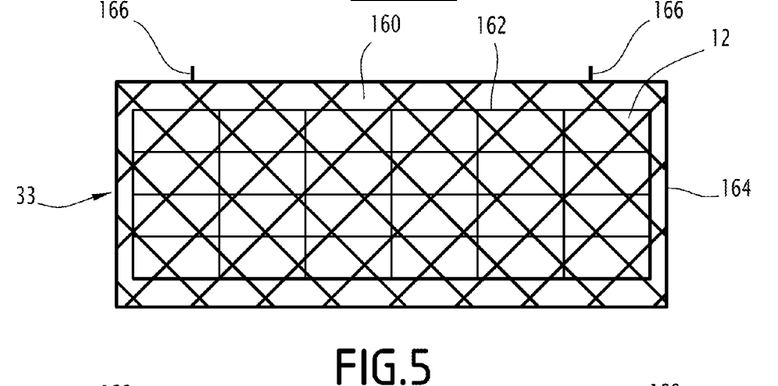
FIG. 5 is a side view of a container which is intended to receive a plurality of pallets which are transported through the sterilisation installation according to the invention.

In the example illustrated in FIG. 5, the container 33 has open-work side walls 162 which delimit openings for the passage of the sterilising gas. In that example, the walls 162 are formed by an open-work grill.

The container 33 also comprises a side door 164 for access to the internal volume 160, allowing the pallets 12 to be loaded in the internal volume 160.

The container 33 further comprises holding means 166 which are formed, for example, by rings which are mounted on the upper wall thereof.

The guiding path 152 is arranged above the enclosures 44, 90, 110. It extends linearly along the movement axis A-A' opposite and above the input station 20, the pre-processing station 22, the sterilisation station 24, the desorption station 26 and the output station 28.

The length of the guiding path 152 is thus greater than several meters, advantageously greater than several tens of meters.

The guiding path 152 thus comprises two longitudinal guiding rails 170 which are carried by vertical posts 172. The rails 170 and the posts 172 are arranged at one side and the other of the axis A-A', transversely relative to the vessels 50A, 50B, 50C.

The width which transversely separates the rails 170 is substantially equal to the width of each vessel 50A, 50B, 50C. That width is greater than 1 m and is, for example, between 1 m and 20 m, advantageously between 5 m and 15 m.

The height which separates the rails 170 from the upper edge 60 when the cover 52A, 52B, 52C occupies its position for access to the chamber 56A, 56B, 56C is substantially equal to or greater than the height of the container 33.

The guiding path 152 extends opposite the input plate 42 in the input station 20. Subsequently, it extends above the pre-processing vessels 50A, then into the confined volume 140 through the upstream lock chamber 142 in order to extend successively above the sterilisation vessels 50B and the desorption vessels 50C.

Subsequently, it extends out of the confinement volume 140 through the downstream lock chamber 144 and extends opposite the output plate 130 of the station 28.

The guided device 154 comprises a travelling platform 174 which is guided by the rails 170, means 176 for vertical movement of the containers 33 carried by the travelling platform 174 and means 177 for propelling the travelling platforms 174 along the guiding path 152.

The platform 174 extends transversely between the rails 170. It is capable of travelling on the rails 170 along the axis A-A' in order to pass successively opposite the stations 20 to 28. In this manner, it is movable only in translation along the axis A-A', its trajectory being controlled by the guiding path 152.

The platform 174 has a width substantially equal to the distance separating the rails 170. It is provided with means 178 for moving on the rails 170.

The vertical movement means 176 comprise at least a traction winch 180 for the container 33. The winch 180 is provided with holding lines 182 which are capable of becoming releasably engaged with the holding means 166 located on the container 33.

When the holding lines 182 are engaged with the holding means 166, the winch 180 is capable of carrying the container 33 and moving it vertically between a lower position for being loaded in a enclosure 50A, 50B, 50C and an upper position for transport between the stations 20 to 28, in which the container 33 can be moved together with the guided device 154 above the vessels 50A, 50B, 50C.

The propulsion means 177 are capable of moving the movable platform 174 along the guiding path 152 in two opposing directions along the axis A-A'.

The control means 156 are capable of activating the propulsion means 177 in order to control the movement of the guided device 154 over the guiding path 152. They are capable of carrying out a sequence for taking a container 33 at the input station 20, moving the container 33 containing the pallets 12 of objects to be sterilised successively into the pre-processing station 22, the sterilisation station 24 and the desorption station 26, then a sequence for unloading the container 33 at the output station 28.

The control means 156 advantageously comprise safeguarding means which prevent a container 33 from moving to the output station 28 if it has not been subjected to sterilisation in the sterilisation station 24.

A first method for sterilising a plurality of objects in the installation 10 will now be described.

Initially, the pallets 12 which contain the objects to be sterilised are unloaded from the lorry 43 at the unloading platform 40. They are subsequently transported in a container 33 which has been emptied beforehand and are introduced into the internal volume 160 of that container 33 with the access door 164 being opened.

The container 33 is positioned on the input plate 42 and is positioned transversely relative to the axis A-A'.

The guided device 154 is moved opposite and above the container 33 in the input station 20.

To that end, it is moved under the effect of the propulsion means 177 and is guided on the rails 170 along the axis A-A'. When the travelling platform 174 is located above the container 33, the movement means 176 are activated. The winch 180 is controlled to lower the holding lines 182 and to connect the holding lines 182 to the holding means 166 of the container 33.

The container 33 is raised as far as an upper movement position, in which its lower surface is located at a height greater than the height of the upper surface of the covers 52A, 52B, 52C.

With reference to FIG. 3, the first jacks 74 of the pre-processing enclosure 44 are subsequently activated in order to raise the movable rails 70 and to position them opposite the fixed rails 72.

During that movement, the movement members 66 of the cover 52A move into contact with the movable rails 70, which allows the cover 52A to be raised away from and above the edge 60.

The second jack 76 is activated in order to move the cover 52A transversely from its closure position to its access position, with the movement members 66 being moved on the rails 70, 72.

As illustrated in FIGS. 2 and 4, the upper opening 58 is free. The travelling platform 174 is moved in a downstream direction along the guiding path 152 in order to place the container 33 above the upper opening 58. Subsequently, the winch 180 is activated in order to lower the container 33 towards its lower position and to load it in the pre-processing chamber 56A.

When the container 33 rests on the bottom of the chamber 56A, the lines 182 are disengaged from the holding means 166.

Subsequently, the second jack 76 is controlled to move the cover towards its closure position. The movable rails 70 are lowered again by the first vertical jacks 74 in order to position the cover on the edge 60 and to close the chamber 56A in a sealed manner.

The means 46 for adjusting the temperature and the means 48 for adjusting the hygrometry are activated to bring about, in the chamber 56A, relative humidity of approximately between 40% and 100% at a temperature between 30° C. and 60° C. for a period of time greater than two hours and particularly of substantially eight hours.

When the pre-processing is finished, the cover 52A is moved into its position for access to the chamber 56A as described above. The winch 180 is again activated to connect the lines 182 to the holding means 166 and to remove the container 33 from the chamber 56A by drawing it vertically towards its upper position.

The container 33 is moved together with the guided device 154 along the axis A-A' towards the sterilisation station 24.

During that movement, the container 33 is introduced into the confinement volume 140 through the upstream lock chamber 142.

It is then arranged opposite a sterilisation vessel 50B. As described above, the cover 52B is moved into the position for access to the sterilisation chamber 56B. The container 33 is lowered into the sterilisation chamber 56B and the cover 52B is closed again by the movement means 54B in order to close the chamber 56B in a sealed manner.

Once the cover 52B has been closed again, a high vacuum is first brought about in the sterilisation chamber 56B by activating the vacuum pump and opening the control valve 102 of the draining conduit 100.

The sterilising gas is introduced through the introduction conduit 96 by opening the valve 98 in order to create an atmosphere containing at least 0.1%, advantageously at least 1%, of sterilising gas in the sterilisation chamber 56B for a period of time greater than two hours and in particular substantially of eight hours.

Subsequently, when the sterilisation is carried out, the vacuum pump is activated and the draining valve 102 is opened in order to completely remove the gas contained in the sterilisation chamber 56B.

The pressure in the chamber 56B is again increased and the cover 52B is opened. The traction means 180 raise the container 33 in order to remove it from the sterilisation chamber 56B.

The container 33 is moved by the guided device 154 above the vessels 90 towards the desorption station 26 along the guiding path 152.

The cover 52C of a desorption enclosure 50C is opened by the movement means 54C, as described above. The guided device 154 is moved opposite the desorption chamber 56C and the container 33 is lowered into the chamber 56C.

Subsequently, the cover 52C is moved to close the desorption chamber 56C in a sealed manner.

Draining gas is injected into the chamber 56C several times by means of the injection conduit 116 by opening the valve 118. Each injection is followed by a desorption cycle using a vacuum pump by opening the valve 122 which is provided on the draining conduit 120.

After a period of time of at least four hours and in particular thirty-six hours, the cover 56C is opened and the guided device 154 is positioned opposite the desorption chamber 56C.

The winch 180 is activated to raise the container 33 out of the desorption chamber 56C by means of the lines 182.

Subsequently, the device 154 is moved downstream over the guiding path 152 and leaves the confinement volume 140 by means of the downstream lock chamber 144.

When the guided device 154 reaches the output station, it unloads the container 33 either in a storage region 132 or in the movable vehicle 134 which allows the sterilised objects to be transported away from the installation 10 out of the building 18.

The movement of the guided device 154 between the various stations 20 to 28 is controlled automatically by the control means 156.

Therefore, the installation 10 according to the invention allows all of the steps of the sterilisation method to be carried out with minimal handling and in a reliable and controlled manner.

In this manner, only two handling steps are necessary, that is to say, loading the pallets 12 of objects to be sterilised from the lorries 43 into the container 33, and transporting the pallets 12 of sterilised objects out of the building 18 from the output station 28.

Therefore, it is possible to reduce the time and operators necessary for carrying out the sterilisation, which substantially reduces the cost, particularly when the volumes of objects to be sterilised are high.

Furthermore, the presence of a confinement wall 30 which delimits a confinement volume 140 prevents the exposure of the operators to the sterilising gas which improves the security of the installation 10.

Since the enclosures 44, 90, 110 are arranged side by side along the axis A-A', the space taken up by the installation 10 in the building 18 is minimal.

The presence of control means 156 provided with safeguarding means further ensures great reliability of the sterilisation because those means prevent non-sterile objects from reaching the output station 28.

Figure 6:
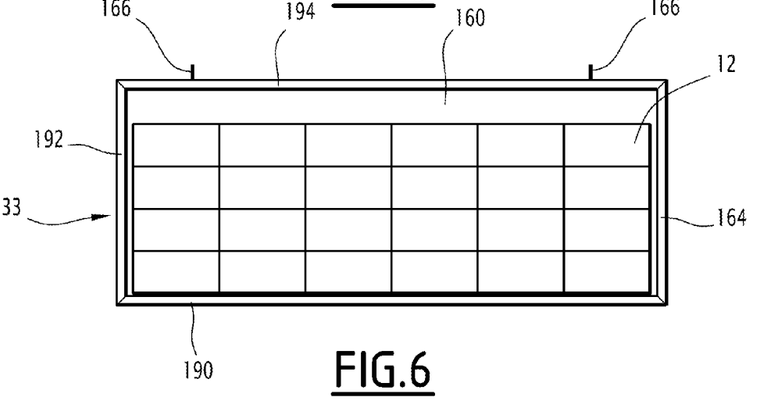
FIG. 6 is a view, similar to FIG. 5, of a container variant.

In a variant illustrated in FIG. 6, the container 33 comprises a lower plate 190 for supporting the pallets 12 and a frame comprising four vertical pillars 192 which are arranged at the corners of the plate 190. The vertical pillars 192 together delimit lateral openings which are completely free.

The holding members 166 are arranged either on an upper plate 194 or on cross-members which connect the pillars 192 at the upper ends thereof.

Figure 7:
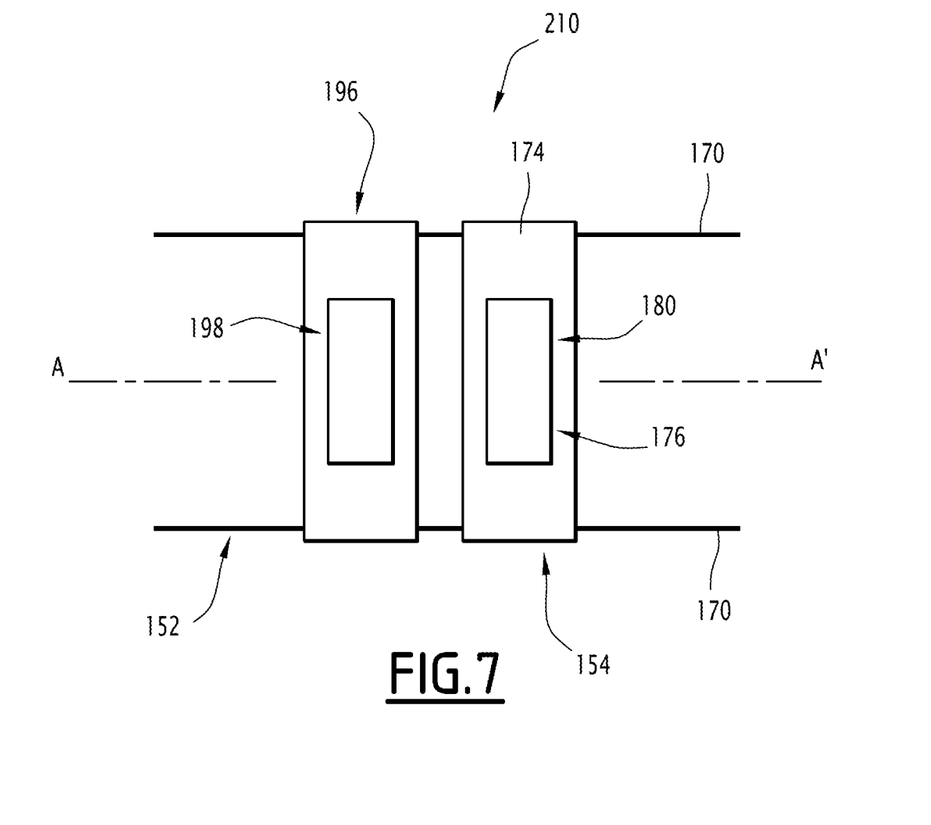
FIG. 7 is a partial top view of the guided device of a second installation according to the invention.

A second installation 210 according to the invention is illustrated in FIG. 7.

Unlike the first installation 10, the means 54A, 54B, 54C for moving each cover 52A, 52B, 52C are formed by an auxiliary guided device 196 which is mounted on the guiding path 152 downstream of the guided device 154.

The auxiliary guided device 196 is separate from the guided device 154. Similarly to the guided device 154, it carries a winch 198 which is capable of raising each cover 52A, 52B, 52C and displacing it longitudinally from the vessel 50A, 50B, 50C on which it rests in order to release access to the chamber 56A, 56B, 56C, respectively.

The operation of the second installation 210 differs from the operation of the first installation 10 in that, in order to move into the position for access to the chamber 56A, 56B, 56C, the cover 52A, 52B, 52C is raised by the winch 198 of the auxiliary guided device 196 and is displaced longitudinally relative to the opening 58 before introducing the container 33 into an enclosure 44, 90, 110.

The invention claimed is:

1. An installation for sterilizing a plurality of objects, the installation comprising:
   an input station which is capable of receiving the plurality of objects to be sterilized;
   a sterilization station which comprises at least one sterilization enclosure which is intended to receive the plurality of objects, the sterilization station comprising at least one means for introducing a sterilizing fluid into the sterilization enclosure and at least one means for discharging the sterilizing fluid;
   a desorption station for desorbing the sterilizing fluid from the plurality of objects, comprising at least one desorption enclosure, the desorption station comprising at least one means for draining the desorption enclosure;
   an output station which is capable of receiving the plurality of objects after sterilization;
   a transport means which is for transporting the plurality of objects and which is capable of successively moving the plurality of objects from the input station into the sterilization station and into the desorption station as far as the output station;
   wherein the transport means comprises:
   a continuous guiding path, the input station, the sterilization station, the desorption station and the output station (28) being arranged successively opposite the guiding path; and
   at least one guided device which is guided by the guiding path,
   the guided device comprising movement means for moving the plurality of objects relative to the guided device between a position for common movement of the plurality of objects and the guided device along the guiding path and a position for insertion of the plurality of objects in each of the sterilization enclosure and the desorption enclosure.

2. The installation according to claim 1, further comprising at least one container which delimits a volume for receiving the plurality of objects, wherein the container comprises at least one member for releasable connection to the movement means.

3. The installation according to claim 1, wherein the guiding path is located above the sterilization enclosure and above the desorption enclosure, and wherein the sterilization enclosure and the desorption enclosure open upwards opposite the guiding path.

4. The installation according to claim 3, wherein the guided device comprises a travelling platform, the movement means comprising at least one traction member which is carried by the travelling platform and which is capable of lowering the plurality of objects into the sterilization enclosure and into the desorption enclosure, and of raising the plurality of objects in order to remove the plurality of objects from the sterilization enclosure and the desorption enclosure.

5. The installation according to claim 1, wherein the sterilization enclosure and the desorption chamber each delimit a single access opening for inserting and removing the plurality of objects.

6. The installation according to claim 1, wherein the guiding path extends linearly between the input station and the output station, the sterilization station and the desorption station being located side by side along the guiding path between the input station and the output station.

7. The installation according to claim 6, wherein the sterilisation station comprises a plurality of sterilization enclosures, the desorption station comprising a plurality of desorption enclosures, the sterilization enclosures and the desorption enclosures being arranged successively side by side in an adjacent manner along the guiding path.

8. The installation according to claim 1, further comprising a pre-processing station which is arranged upstream of the sterilization station along the guiding path, wherein the pre-processing station comprises at least one pre-processing enclosure and means for controlling the humidity and/or the temperature in the pre-processing enclosure.

9. The installation according to claim 1, further comprising a confinement wall which delimits a confinement volume, the sterilization station and the desorption station being located in the confinement volume, the input station and the output station being located outside the confinement volume,
wherein the confinement wall delimits an upstream lock chamber and a downstream lock chamber opening in the confinement volume, and
wherein the guiding path extends successively through the upstream lock chamber, the confinement volume and the downstream lock chamber.

10. The installation according to claim 1, wherein the output station comprises at least one moving vehicle which delimits a surface for loading the plurality of objects that are sterilized, the moving vehicle being movable between a position for receiving the plurality of objects, in which the loading surface extends opposite the guiding path in order to be loaded by the transport means, and a position remote from the guiding path.

11. The installation according to claim 1, wherein the sterilisation enclosure delimits a sterilization chamber which is capable of receiving the plurality of objects and comprises a lid for sealingly closing the sterilization chamber, the sterilization station comprising means for moving the lid which is capable of moving the lid between a position for access to the sterilization chamber and a position for closing the sterilization chamber.

12. The installation according to claim 11, wherein, in the access position, the sterilization chamber opens opposite the guiding path, the lid being transversely displaced relative to the guiding path.

13. The installation according to claim 11, wherein the means for moving the lid comprises an auxiliary device which is guided by the guiding path.

14. A method for sterilizing a plurality of objects in an installation, according to claim 1, the method comprising:
taking, by the movement means carried by the guided device, the plurality of objects from the input station;
moving the guided device over the guiding path in order to place the guided device opposite to the sterilization station;
introducing, by the movement means carried by the guided device, the plurality of objects into the sterilization enclosure;
injecting sterilizing fluid into the sterilizing enclosure to sterilize the plurality of objects in the sterilization enclosure;
removing, by the movement means carried by the guided device, the plurality of objects from the sterilization enclosure;
moving the guided device over the guiding path to place the guided device opposite to the desorption station;
introducing, by the movement means carried by the guided device, the plurality of objects into the desorption enclosure;
desorption of the sterilizing fluid from the plurality of objects in the desorption enclosure;
removing, by the movement means carried by the guided device, the plurality of objects from the desorption enclosure;
moving the guided device over the guiding path as far as the output station;
depositing, by the movement means carried by the guided device, the plurality of sterilized objects in the output station.

* * * * *